United States Patent
Shepherd et al.

(10) Patent No.: US 8,816,861 B2
(45) Date of Patent: Aug. 26, 2014

(54) SYSTEM AND METHOD FOR DATA ANOMALY DETECTION PROCESS IN ASSESSMENTS

(71) Applicant: Questionmark Computing Limited, London (GB)

(72) Inventors: Eric Shepherd, Miami Beach, FL (US); John Kleeman, London (GB)

(73) Assignee: Questionmark Computing Limited, London (GB)

( * ) Notice: Subject to any disclaimer, the term of this patent is extended or adjusted under 35 U.S.C. 154(b) by 69 days.

(21) Appl. No.: 13/667,425

(22) Filed: Nov. 2, 2012

(65) Prior Publication Data

US 2013/0113628 A1    May 9, 2013

Related U.S. Application Data

(60) Provisional application No. 61/555,748, filed on Nov. 4, 2011.

(51) Int. Cl.
 *G08B 23/00*    (2006.01)

(52) U.S. Cl.
 USPC ............... 340/573.1; 340/539.1; 340/500; 600/301; 600/544; 600/558

(58) Field of Classification Search
 USPC ........... 340/573.1, 539.1, 539.12, 573.3, 500; 600/300, 301, 306, 544, 558, 657; 702/19, 20, 179; 128/903, 904, 920
 See application file for complete search history.

(56) References Cited

U.S. PATENT DOCUMENTS

| | | | | |
|---|---|---|---|---|
| 7,565,193 | B2* | 7/2009 | Laken | 600/544 |
| 8,244,475 | B2* | 8/2012 | Aguilar et al. | 702/19 |
| 2003/0130595 | A1* | 7/2003 | Mault | 600/567 |
| 2010/0185113 | A1* | 7/2010 | Peot et al. | 600/544 |

OTHER PUBLICATIONS

Kleeman, John, "Recent cognitive psychology research shows strongly that quizzes help retain learning. What does this mean for CAA?", International Computer Assisted Assessment (CAA) Conference, (2011), pp. 1-12.

Frequently asked questions, http://www.media.mit.edu/galvactivator/faq.html, (downloaded on Mar. 21, 2014), pp. 1-4.

Emotive EPOC—EPOC Specifications, Brain Computer Interface Technology, Emotiv (2012), 4 pages.

Denot-Ledunois, et al., "The effect of attentional load on the breathing pattern in children", International Journal of Psychophysiology 29 (1998) 13-21.

SWOV Fact sheet "Attention problems behind the wheel" SWOV Institute for Road Safety Research, (Feb. 2012), pp. 1-6.

(Continued)

*Primary Examiner* — Hung T. Nguyen
(74) *Attorney, Agent, or Firm* — Brian J. Colandreo; Michael T. Abramson; Holland & Knight LLP

(57) ABSTRACT

A method, computer program product, and computer system for detecting cheating in an assessment. Brainwaves of a user are identified. An attention level of the user is determined with the identified brainwaves. The attention level of the user is analyzed. An action of the user is classified as a cheating event using the analyzed attention level of the user.

21 Claims, 3 Drawing Sheets

(56) References Cited

OTHER PUBLICATIONS

Ravaja, Niklas, "Presence-Related Influences of a Small Talking Facial Image on Psychophysiological Measures of Emotion and Attention", Proceedings of the 5th Annual International Workshop Presence, (Oct. 9, 2002), 8 pages.

Bolls, et al., "The Effects of Message Valence and Listener Arousal on Attention, Memory, and Facial Muscular Responses to Radio Advertisements", Communication Research, vol. 28 No. 5, (Oct. 2001), pp. 627-651.

"Are You Really Paying Attention? Doppler Sonography Helps Psychologists Measure Attention Levels", http://old.sciencedaily.com/videos/2006/1212-are_you_really_paying_attention.htm, ScienceDaily, (Dec. 1, 2006), 3 pages.

MindWave headset, NeuroSky, http://store.neurosky.com/products/mindwave-1, (downloaded on Mar. 8, 2012), 3 pages.

* cited by examiner

| Action | Actual Attention Level | Control Attention Level | Difficulty Level | Actual Time (m) | Control Time (m) | Cheat Event Alert | |
|---|---|---|---|---|---|---|---|
| 1 | 1 | 5 | X | X | X | + | Y |
| 2 | 3 | 8 | 0.2 | X | X | + | Y |
| 3 | 3 | 8 | 0.2 | 1 | 9 | + | Y |
| 4 | 5 | 5 | 0.9 | X | X | + | Y |
| . | . | . | . | . | . | . | . |
| . | . | . | . | . | . | . | . |
| . | . | . | . | . | . | . | . |
| n | n | n | n | n | n | n | n |

FIG. 3

SYSTEM AND METHOD FOR DATA ANOMALY DETECTION PROCESS IN ASSESSMENTS

RELATED CASES

This application claims the benefit of U.S. Provisional Application No. 61/555,748, filed on 4 Nov. 2011, the contents of which are hereby incorporated by reference.

TECHNICAL FIELD

This disclosure relates to assessment systems and methods and, more particularly, to assessment cheating detection systems and methods.

BACKGROUND

Assessments (e.g., exams) are used in many parts of society to measure knowledge, skills, abilities and behaviors, e.g., in order to certify people for job roles and qualifications or grant licenses to work or perform tasks. For instance, educational institutions may use exams to validate work, knowledge, and skills to give educational qualifications. As another example, during the recruitment or promotion processes, an organization may test how a candidate behaves under certain circumstances to see if the candidate will fit in with the culture. As yet another example, companies including Information Technology (IT) and other high-tech companies may issue certifications to people who can use or maintain products, or who are skilled with products. Organizations may use internal exams to confirm that people are competent to do jobs where failure has a high risk (e.g., financial services and trading, operators of power stations and transport operators, etc.). Government agencies may provide licenses-to-work based on exam results for many professional trades such as doctors, nurses, crane operators, etc., and for licenses to drive.

Some of these exams may be delivered by paper and/or remotely by computer, with a candidate using, e.g., a workstation or other device to answer questions. Part of the process of conducting an exam may be to minimize cheating. Common forms of cheating may include, for example, identity fraud (e.g., where someone other than the candidate claims to be the candidate), use of cheating materials (e.g., having access to books, the internet, or other resources in a closed-book exam), prompting another person giving the right answer (e.g., someone sitting by the candidate or via telephone), and copying answers (e.g., looking at how others taking the exams at the same time are answering questions and using the same answers).

There are many variants of cheating and with exams where little, inadequate, or no supervision is provided to the candidate, cheating may be a problem where society may not fully trust the integrity of the certifications, qualifications and licenses that the exams provide.

SUMMARY OF DISCLOSURE

In one implementation, a method for detecting cheating in an assessment, performed by one or more computing devices, comprises identifying brainwaves of a user. An attention level of the user is determined with the identified brainwaves. The attention level of the user is analyzed. An action of the user is classified as a cheating event using the analyzed attention level of the user.

One or more of the following features may be included. Analyzing the attention level of the user may include comparing the attention level of the user with a second attention level, wherein the second attention level may be from at least one of the user and a second user. Analyzing the attention level of the user may include comparing the attention level of the user with a difficulty level of the action of the user. Analyzing the attention level of the user may further include comparing an amount of time spent by the user to perform the action with the difficulty level of the action.

Analyzing the attention level of the user may include identifying the action of the user as requiring the attention level of the user to reach a threshold attention level, and determining that the attention level of the user is less than the threshold attention level for the action of the user. The action of the user may include answering one or more questions. An alert of the cheating event may be provided to at least one of the user and a second user.

In another implementation, a computer program product resides on a computer readable medium that has a plurality of instructions stored on it. When executed by a processor, the instructions cause the processor to perform operations comprising identifying brainwaves of a user. An attention level of the user is determined with the identified brainwaves. The attention level of the user is analyzed. An action of the user is classified as a cheating event using the analyzed attention level of the user.

One or more of the following features may be included. Analyzing the attention level of the user may include comparing the attention level of the user with a second attention level, wherein the second attention level may be from at least one of the user and a second user. Analyzing the attention level of the user may include comparing the attention level of the user with a difficulty level of the action of the user. Analyzing the attention level of the user may further include comparing an amount of time spent by the user to perform the action with the difficulty level of the action.

Analyzing the attention level of the user may include identifying the action of the user as requiring the attention level of the user to reach a threshold attention level, and determining that the attention level of the user is less than the threshold attention level for the action of the user. The action of the user may include answering one or more questions. An alert of the cheating event may be provided to at least one of the user and a second user.

In another implementation, a computing system includes a processor and memory configured to perform operations comprising identifying brainwaves of a user. An attention level of the user is determined with the identified brainwaves. The attention level of the user is analyzed. An action of the user is classified as a cheating event using the analyzed attention level of the user.

One or more of the following features may be included. Analyzing the attention level of the user may include comparing the attention level of the user with a second attention level, wherein the second attention level may be from at least one of the user and a second user. Analyzing the attention level of the user may include comparing the attention level of the user with a difficulty level of the action of the user. Analyzing the attention level of the user may further include comparing an amount of time spent by the user to perform the action with the difficulty level of the action.

Analyzing the attention level of the user may include identifying the action of the user as requiring the attention level of the user to reach a threshold attention level, and determining that the attention level of the user is less than the threshold attention level for the action of the user. The action of the user may include answering one or more questions. An alert of the cheating event may be provided to at least one of the user and a second user.

The details of one or more implementations are set forth in the accompanying drawings and the description below. Other features and advantages will become apparent from the description, the drawings, and the claims.

BRIEF DESCRIPTION OF THE DRAWINGS

FIG. 3 is an illustrative table containing information that may be used by the data anomaly detection process of FIG. 1.

Like reference symbols in the various drawings indicate like elements.

DETAILED DESCRIPTION OF THE EMBODIMENTS

System Overview

Figure 1:
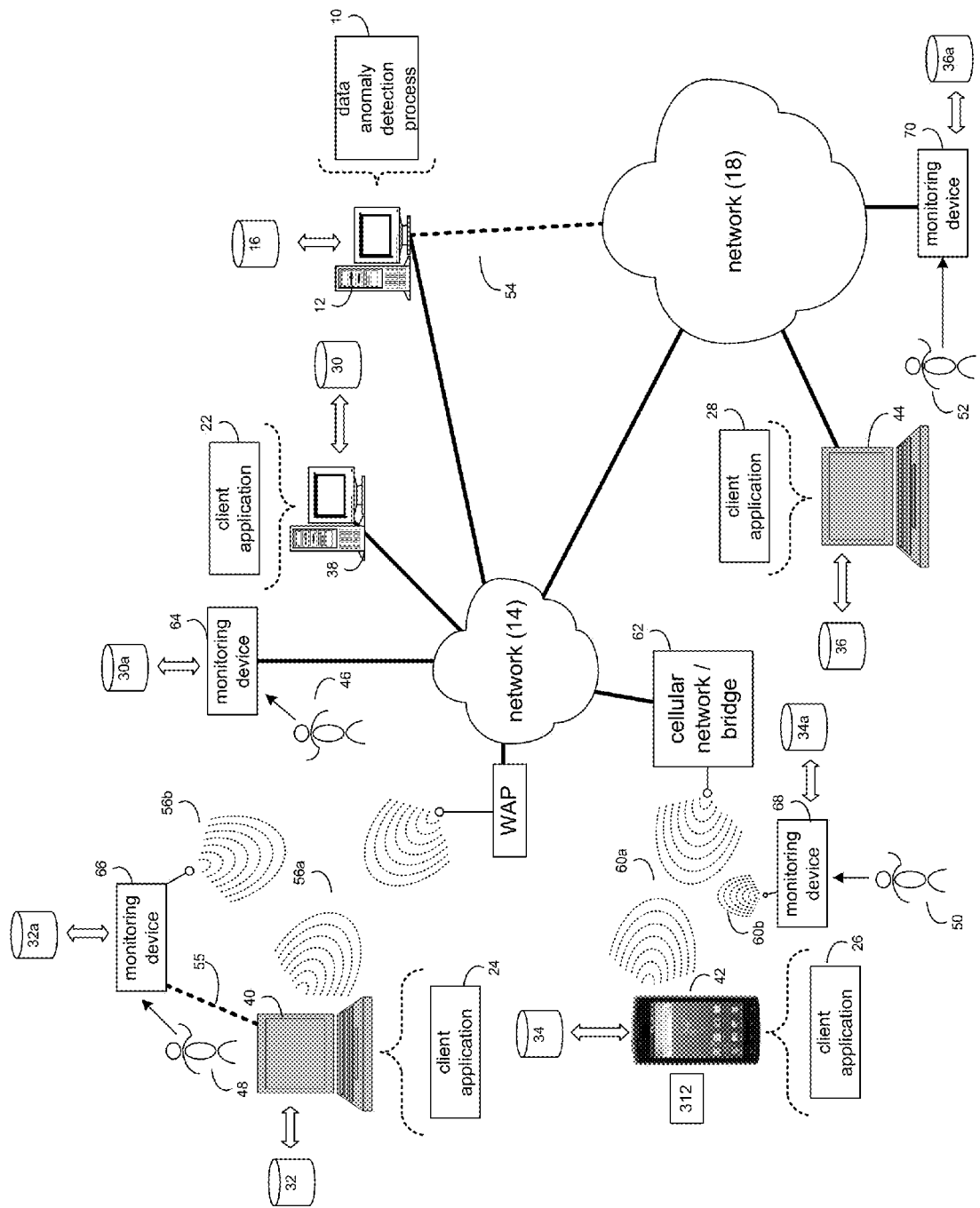
FIG. 1 is an illustrative diagrammatic view of a data anomaly detection process coupled to a distributed computing network.

As will be appreciated by one skilled in the art, the present disclosure may be embodied as a method, system, or computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer readable medium may be a computer readable signal medium or a computer readable storage medium. The computer-usable, or computer-readable, storage medium (including a storage device associated with a computing device or client electronic device) may be, for example, but not limited to, an electronic, magnetic, optical, electromagnetic, infrared, or semiconductor system, apparatus, device, or any suitable combination of the foregoing. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a media such as those supporting the internet or an intranet, or a magnetic storage device. Note that the computer-usable or computer-readable medium could even be a suitable medium upon which the program is stored, scanned, compiled, interpreted, or otherwise processed in a suitable manner, if necessary, and then stored in a computer memory. In the context of this document, a computer-usable or computer-readable, storage medium may be any tangible medium that can contain or store a program for use by or in connection with the instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. The computer readable program code may be transmitted using any appropriate medium, including but not limited to the internet, wireline, optical fiber cable, RF, etc. A computer readable signal medium may be any computer readable medium that is not a computer readable storage medium and that can communicate, propagate, or transport a program for use by or in connection with an instruction execution system, apparatus, or device.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the internet using an Internet Service Provider).

The present disclosure is described below with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by one or more computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks or combinations thereof.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks or combinations thereof.

The computer program instructions may also be loaded onto a computer or other programmable data processing apparatus to cause a series of operational steps to be performed (not necessarily in a particular order) on the computer or other programmable apparatus to produce a computer implemented process such that the instructions which execute on the computer or other programmable apparatus provide steps for implementing the functions/acts (not necessarily in a particular order) specified in the flowchart and/or block diagram block or blocks or combinations thereof.

Referring to FIG. 1, there is shown data anomaly detection process 10 that may reside on and may be executed by computer 12, which may be connected to network 14 (e.g., the internet or a local area network). Examples of computer 12 may include but are not limited to a single server computer, a series of server computers, a single personal computer, a series of personal computers, a mini computer, a tablet computer, a mainframe computer, or a computing cloud. The various components of computer 12 may execute one or more operating systems, examples of which may include but are not limited to: Microsoft Windows Server™; Novell Netware™; Redhat Linux™, Unix, Mobile phone or tablet OS, or a custom operating system, for example.

As will be discussed below in greater detail, data anomaly detection process 10 may detect cheating, e.g., in an assessment. For example, brainwaves of a user may be identified, e.g., via monitoring device 64, 66, 68, 70. An attention level of the user may be determined with the identified brainwaves. The attention level of the user may be analyzed. An action of the user may be classified as a possible data anomaly (e.g., cheating) event using the analyzed attention level of the user.

The instruction sets and subroutines of data anomaly detection process 10, which may be stored on storage device 16 coupled to computer 12, may be executed by one or more processors (not shown) and one or more memory architectures (not shown) included within computer 12. Storage device 16 may include but is not limited to: a hard disk drive; a flash drive, a tape drive; an optical drive; a RAID array; a random access memory (RAM); and a read-only memory (ROM).

Network 14 may be connected to one or more secondary networks (e.g., network 18), examples of which may include but are not limited to: a local area network; a wide area network; or an intranet, for example.

Computer 12 may include a data store, such as a database (e.g., relational database) (not shown) and may be located within any suitable memory location, such as storage device 16 coupled to computer 12. In some embodiments, computer 12 may utilize a database management system such as, but not limited to, "My Structured Query Language" (MySQL) in order to provide multi-user access to one or more databases, such as the above noted relational database. The data store may also be a custom database, such as, for example, a flat file database or an XML database. Any other form(s) of a data storage structure may also be used. Data anomaly detection process 10 may be a component of the database, a stand alone application that interfaces with the above noted data store and/or an applet/application that is accessed via client applications 22, 24, 26, 28. The above noted data store may be, in whole or in part, distributed in a cloud computing topology. In this way, computer 12 and storage device 16 may refer to multiple devices, which may also be distributed throughout the network.

Data anomaly detection process 10 may be accessed via client applications 22, 24, 26, 28. Examples of client applications 22, 24, 26, 28 may include but are not limited to an assessment application, monitoring device application, standard and/or mobile web browser, email client application, a customized web browser, or a custom application. The instruction sets and subroutines of client applications 22, 24, 26, 28, which may be stored on storage devices 30 and/or 30a, 32 and/or 32a, 34 and/or 34a, 36 and/or 36a coupled to client electronic devices 38, 40, 42, 44 and/or monitoring devices 64, 66, 68, 70, may be executed by one or more processors (not shown) and one or more memory architectures (not shown) incorporated into client electronic devices 38, 40, 42, 44 and/or monitoring devices 64, 66, 68, 70.

Storage devices 30, 30a, 32, 32a, 34, 34a, 36, 36a may include but are not limited to: hard disk drives; flash drives, tape drives; optical drives; RAID arrays; random access memories (RAM); and read-only memories (ROM). Examples of client electronic devices 38, 40, 42, 44 may include, but are not limited to, personal computer 38, laptop computer 40, smart phone 42, notebook computer 44, a tablet (not shown), a server (not shown), a data-enabled, cellular telephone (not shown), a television (not shown) with one or more processors embedded therein or coupled thereto, and a dedicated network device (not shown). Additionally/alternatively, client electronic devices 38, 40, 42, 44 may include a monitoring device (e.g., monitoring device 64, 66, 68, 70).

One or more of client applications 22, 24, 26, 28 may be configured to effectuate some or all of the functionality of data anomaly detection process 10 and/or may include at least some of data anomaly detection process 10. Accordingly, data anomaly detection process 10 may be a purely server-side application, a purely client-side application, or a hybrid server-side/client-side application that is cooperatively executed by one or more of client applications 22, 24, 26, 28 and data anomaly detection process 10.

Users 46, 48, 50, 52 and/or monitoring devices 64, 66, 68, 70 may access computer 12 and data anomaly detection process 10 directly through network 14 or through secondary network 18. Further, computer 12 may be connected to network 14 through secondary network 18, as illustrated with phantom link line 54. Data anomaly detection process 10 may include one or more user interfaces, such as browsers and textual or graphical user interfaces, through which users 46, 48, 50, 52 and/or monitoring devices 64, 66, 68, 70 may access data anomaly detection process 10.

The various client electronic devices and/or monitoring devices 64, 66, 68, 70 may be directly or indirectly coupled to network 14 (or network 18). For example, personal computer 38 and monitoring device 64 are shown directly coupled to network 14 via a hardwired network connection. Further, notebook computer 44 and monitoring device 70 are shown directly coupled to network 18 via a hardwired network connection. Laptop computer 40 and monitoring device 66 are shown wirelessly coupled to network 14 via wireless communication channels 56a and 56b respectively established between laptop computer 40 and wireless access point (i.e., WAP) 58 and between monitoring device 66 and WAP 58, which is shown directly coupled to network 14. WAP 58 may be, for example, an IEEE 802.11a, 802.11b, 802.11g, Wi-Fi, and/or Bluetooth™ device that is capable of establishing wireless communication channel 56a between laptop computer 40 and WAP 58 and wireless communication channel 56b between monitoring device 66 and WAP 58. Additionally/alternatively, a monitoring device (e.g., monitoring device 66) may be directly (and/or wirelessly) coupled to a client electronic device (e.g., client electronic device 40) as illustrated with phantom link line 55. Thus, information may be communicated from a monitoring device (e.g., monitoring device 66) to a client electronic device (e.g., client electronic device 40), where the information may be communicated, e.g., to computer 12 via, e.g., a network (e.g., network 14). Smart phone 42 and monitoring device 68 are shown wirelessly coupled to network 14 via wireless communication channels 60a and 60b respectively established between smart phone 42 and cellular network/bridge 62 and monitoring device 68 and cellular network/bridge 62, which is shown directly coupled to network 14.

As is known in the art, all of the IEEE 802.11x specifications may use Ethernet protocol and carrier sense multiple access with collision avoidance (i.e., CSMA/CA) for path sharing. The various 802.11x specifications may use phase-shift keying (i.e., PSK) modulation or complementary code keying (i.e., CCK) modulation, for example. As is known in the art, Bluetooth™ is a telecommunications industry specification that allows, e.g., mobile phones, computers, smart phones, and other devices (e.g., monitoring devices 64, 66, 68, 70) to be interconnected using a short-range wireless connection.

Client electronic devices 38, 40, 42, 44 may each execute an operating system, examples of which may include but are not limited to Android™, Apple iOS™, Microsoft Windows™, Redhat Linux™, or a custom operating system.

Figure 2:
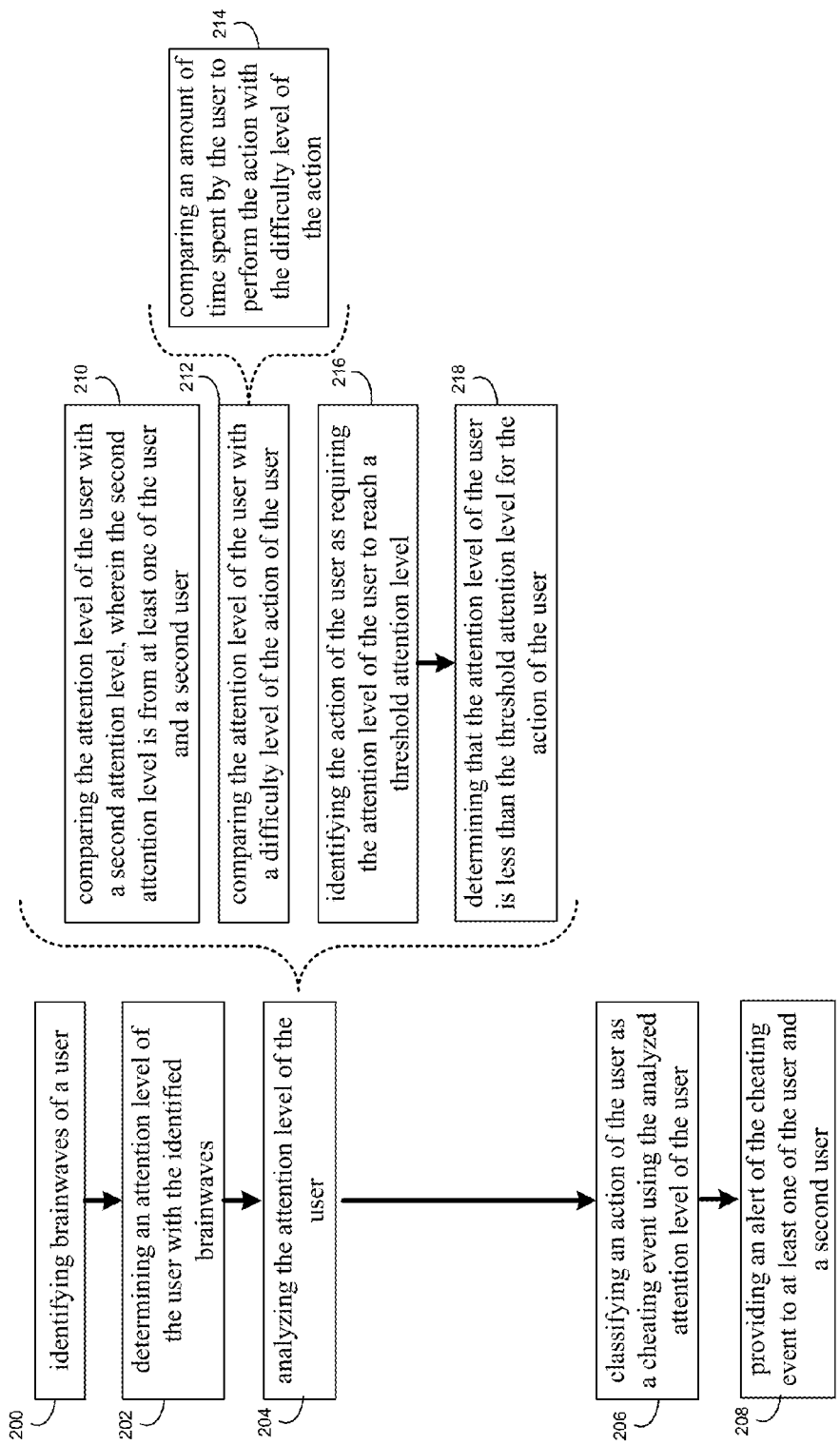
FIG. 2 is an illustrative flowchart of the data anomaly detection process of FIG. 1.

The Data Anomaly Detection Process:

As discussed above and referring also to FIGS. 2-3, data anomaly (e.g., cheating) detection process 10 may detect cheating, e.g., in an assessment. For example, brainwaves of a user (e.g., user 48) may be monitored and/or measured (e.g., via data anomaly detection process 10) and/or subsequently identified 200 by data anomaly detection process 10. This may be achieved, for example, using known brainwave monitoring devices, e.g., monitoring device 66.

The brainwaves of user 48 may be monitored, measured, and identified 200 directly from monitoring device 66 and/or client electronic device 40, e.g., via data anomaly detection process 10. Additionally/alternatively, the brainwaves of user 48 may at any point be recorded on one or more storage devices (e.g., storage device 32 and/or 32a) and/or communicated using any appropriate means noted throughout (e.g., wireless communication channels 56a and 56b, phantom link line 55, etc.) to be recorded on one or more storage devices (e.g., storage devices 16, 30, 30a, 32, 32a, 34, 34a, 36, 36a) and subsequently identified 200 by data anomaly detection process 10. Therefore, any particular description of where and when the brainwaves of user 48 are monitored, measured, identified 200 (and as discussed further below, determined 202, analyzed 204, and classified 206, etc.) by data anomaly detection process 10 using any particular device(s) in any combination should be taken as an example only and not to limit the scope of the disclosure.

An attention level (e.g., attention level 302) of user 48 may be determined 202 by data anomaly detection process 10 with the identified brainwaves. For example, according to one or more example embodiments, monitoring device 66 and/or client electronic device 40 may include the capability to monitor user characteristics of user 48, such as brainwaves and/or heart rate. For instance, the capability of brainwave monitoring may be achieved using, e.g., Electroencephalography (EEG) technology which may measure electronic activity (e.g., varying voltages) within the brain from, e.g., the scalp of user 48. EEG may show oscillations at various frequency ranges. Data anomaly detection process 10 may correlate the frequency ranges and/or special distributions with brain activity. For instance, a low amplitude beta wave of user 48 with multiple and varying frequencies may be associated by data anomaly detection process 10 with various degrees of active thinking, cognitive load, concentration, state of mind, etc. (i.e., attention level). However, those skilled in the art will recognize that other techniques may be used to identify attention level 302 of user 48 using, for example, brainwave monitoring and analysis 204. For example, the raw measurements of the brainwaves may be converted, e.g., by data anomaly detection process 10, into another form (e.g., digital representation) for subsequent analysis 204. As another example, a signature of the brainwaves summarizing attention level 302 and/or 304 of user 48 may be used, e.g., by data anomaly detection process 10, for subsequent analysis 204. As such, the specific description of analyzing 204 the brainwaves may include any combination of the raw brainwaves and any manipulation of the raw brainwaves. As noted above, attention level 302 and/or 304 of user 48 may be analyzed 204 by data anomaly detection process 10 using the brainwaves of user 48. For example, brainwave analysis 204 may allow data anomaly detection process 10 to determine whether user 48 is/was cheating and/or whether there is a high likelihood that user 48 is/was cheating. For example, answering questions may require user 48 to make deductions, calculations, etc., to decide the correct answer properly and fairly, which may require a certain range of attention levels (as indicated, e.g., via identified 200 brainwaves), and if user 48 is/was cheating, the range of attention levels may be noticeably (e.g., measurably) different. For instance, user 48 may be asked identity questions about user 48 and likely may require a low attention level to answer, however, when cheating with identity fraud (e.g., where user 46 takes an exam in place of user 48), user 46 may require a higher attention level to answer the same questions about user 48. As another example, when cheating by user 48 knowing the questions, choices, and correct answers in advance and answering based on memory rather than knowledge, the attention level required by user 48 to answer the question may be minimal. User 48 may also either answer quickly, or if user 48 finishing quickly is a cheater detection method, user 48 may answer quickly and then "daydream" or otherwise think without concentrated attention (i.e., a lower attention level). As another example, cheating by user 48 being prompted by another with the correct answer or copying answers from a fellow test taker, or using a cheat sheet during a closed-book exam, may require a noticeably decreased attention level by user 48. Other cheating techniques may also be attempted by user 48 with varying attention levels being required in the process.

Therefore, consider the following non-limiting examples of data anomaly detection process 10 analyzing 204 attention level 302 of user 48, for example, where user 48 is performing an action (e.g., action 300) of answering questions on an exam:

Analyzing 204 attention level 302 of user 48 by data anomaly detection process 10 may include comparing 210 attention level 302 of user 48 with a second attention level (e.g., control attention level 304), wherein control attention level 304 may be from at least one of user 48 and a second user (e.g., user 48 and/or user 46). For instance, assume for example purposes only that user 48 and the second user are the same user. Further assume for example purposes only that a first exam (e.g., a calibration exercise for user 48 to determine a control norm) was previously taken by user 48 where the attention levels for answering different question types (e.g., easy, medium, hard) are determined 202 (e.g., as control attention level 304) and where the control attention level 304a of user 48 for the difficult question type is determined 202. Further assume for example purposes only that a second exam (e.g., the real exam) is later taken by user 48 where the attention levels for answering the same question types of the first exam are determined 202. Further assume for example purposes only that the control attention level (e.g., 304a) of user 48 answering the hard question (e.g., action 300a) on the first exam is analyzed 204 by data anomaly detection process 10 to be significantly higher than the actual attention level (e.g., 302a) of user 48 answering the hard question on the second exam, action 300a of user 48. The extent of the analyzed 204 difference in attention level may be indicative of a cheating event (e.g., anomaly) where unauthorized help was used by user 48 to significantly lessen the attention level needed to answer the same difficulty question type. As a result, data anomaly detection process 10 may classify 206 action 300a as a possible cheating event using, e.g., attention level(s) 302a and/or 304a of user 48. Those skilled in the art will appreciate that any number of attention levels (and/or their associated averages) for any number of users may be used as a benchmark (e.g., threshold) for the comparison.

Additionally/alternatively, if data anomaly detection process 10 classifies 206, e.g., action 300a, as a cheating event, data anomaly detection process 10 may provide 208 alert 312 (e.g., cheat event alert 312a) of the cheating event to at least one of user 48 and a second user (e.g., user 50 via client electronic device 42). User 50 may include, for example, a monitor (also known as supervisor, proctor or invigilator) or other authority responsible for investigating and ensuring the validity of action 300, and need not be another test taker as illustratively shown.

Data anomaly detection process 10 may classify 206 any action (e.g., 300a) as a possible cheating event, for example, on-the-fly and/or in post-exam analysis. If classified 206 on-the-fly, data anomaly detection process 10 (and/or the supervisor) may stop the exam, where user 48 may be instructed to take the exam at another time (and sometimes in another place or in a more supervised environment). Additionally/alternatively, data anomaly detection process 10 may provide 208 an alert (e.g., alert 312a) to instruct user 50 to check on user 48 or to increase the level of monitoring in person and/or by video (e.g., immediately and/or in the future) or in some other way increase vigilance or gather further data. Additionally/alternatively, if classified 206 by post-test analysis, data anomaly detection process 10 may provide 208 an alert (e.g., alert 312a) to instruct user 50 to monitor user 48 closer in the future. Additionally/alternatively, if no brainwaves are detected, similar action may be taken, since, e.g., otherwise one may avoid the process by, e.g., disabling the monitoring device.

Additionally/alternatively, those skilled in the art will recognize that the second user (e.g., user 46) may be different than user 48. As such, control attention level 304a may be, for example, a comparison between attention level 302a used by user 46 to perform action 300a and attention level 304a used by user 48 to perform action 300a. If the attention level used to perform action 300a differs significantly between users 48 and 46, this may be indicative of a cheating event where unauthorized help was used by one of users 48 and 50 to significantly lessen the attention level needed to answer the same difficulty question type. Additionally/alternatively, those skilled in the art will recognize that the control attention level 304 (e.g., 304a) may be an average of multiple users performing action 300 (e.g., action 300a) within an acceptable attention level limit. Therefore, any particular description of control attention level 304 should be taken as an example only and not to limit the scope of the disclosure.

Additionally/alternatively, data anomaly detection process 10 analyzing 204 attention level 302 of user 48 may include comparing 212 attention level 302 of user 48 with a difficulty level (e.g., difficulty level 306) of action 300 taken by user 48. For example, question difficulty may be measured as, e.g., a number or p value (e.g., as a number from 0 to 1), being the chance of average candidates correctly answering action 300 (so a p value of 0.7 means that 70% of candidates correctly answer). For example, an "easy" question may be a 0.9 difficulty level and a "hard" question may be a 0.2 difficulty level. Other methods of measuring question difficulty (e.g., item response theory) may also be used. Those skilled in the art will appreciate that other techniques of calculating question difficulty may also be used without departing from the scope of the disclosure, and that question difficulty may vary with the test-taker's competence so that a question that is difficult for a beginner may be easy for an expert (e.g., data anomaly detection process 10 may take into account what is the expected cognitive load vs. the actual cognitive load). Generally, harder questions may take longer to answer than easier questions, and harder questions may also require a higher attention level than easier questions. As such, an analysis 204 which compares 212 a user's attention level while performing action 300 (e.g., answering a question) with the difficulty level (e.g., difficulty level 306) may be used by data anomaly detection process 10 to distinguish and to classify 206 a user (e.g., user 48) as cheating and/or having a high probability of cheating. For example, assume for example purposes only that the difficulty level (e.g., difficulty level 306b) of action 300b is high (e.g., 0.2). As such, control attention level 304b of user 48 may on average be high (e.g., around 8 using a scale of 1-10). Further assume for example purposes only that user 48 performs action 300b and data anomaly detection process 10 determines 202 the attention level (attention level 302b) of user 48 for performing action 300b is (e.g., 3). The extent of the analyzed 204 difference in attention level 302b verses difficulty level 306b (and/or control attention level 304b) may be indicative of a cheating event where unauthorized help was used by user 48 to significantly lessen the attention level needed to answer a difficult question (i.e., action 300b). As a result, data anomaly detection process 10 may classify 206 action 300b as a possible cheating event using, e.g., attention level 302b of user 48.

Additionally/alternatively, as noted above, if data anomaly detection process 10 classifies 206 action 300b as a possible cheating event, data anomaly detection process 10 may provide 208 alert 312 (e.g., cheat event alert 312b) of the cheating event to at least one of user 48 and a second user (e.g., user 50 via client electronic device 42).

Additionally/alternatively, data anomaly detection process 10 analyzing 204 attention level 302 of user 48 may further include comparing 214 an amount of time (e.g., actual time 308 and/or control time 310) spent by user 48 to perform action 300 with difficulty level 306 of action 300. For example, data anomaly detection process 10 may more accurately analyze 204 attention level 302 of user 48 if, for example, time (e.g., actual time 308) is also incorporated into the analysis 204. For instance, assume for example purposes only that the difficulty level (e.g., difficulty level 306c) of action 300c is high (e.g., 0.2). As such, control attention level 304c of user 48 may on average be high (e.g., around 8). Further assume for example purposes only that user 48 performs action 300c and data anomaly detection process 10 determines 202 the attention level (attention level 302c) of user 48 for performing action 300c is (e.g., 3). Further assume for example purposes only that user 48 performs action 300c in an amount of time 308c (e.g., 1 minute) that is similar to an amount of time as would be performed with an easier action. The extent of the analyzed 204 difference in attention level 302c versus difficulty level 306c (and/or control attention level 304c) when also compared 214 with amount of time 308c used by user 48 when answering action 300c may be a stronger indication of a cheating event where unauthorized help was used by user 48 to answer a difficult question (i.e., action 300c). As a result, data anomaly detection process 10 may classify 206 action 300c as a possible cheating event using attention level 302c of user 48.

Additionally/alternatively, as noted above, if data anomaly detection process 10 classifies 206 action 300c as a cheating event, data anomaly detection process 10 may provide 208 alert 312 (e.g., cheat event alert 312c) of the cheating event to at least one of user 48 and a second user (e.g., user 50 via client electronic device 42).

Additionally/alternatively, further assume for example purposes only that user 48 performs action 300c in an amount of time 308c (e.g., 1 minute) where a control amount of time (e.g., control time 310c) around which user 48 should spend on average on action 300c is, e.g., 9 minutes. The extent of the analyzed 204 difference in attention level 302c, difficulty level 306c (and/or control attention level 304c), and amount of time 308c used by user 48 when answering action 300c compared 214 with control time 310c may be a stronger indication of a cheating event where unauthorized help was used by user 48 to answer a difficult question (i.e., action 300c). As a result, data anomaly detection process 10 may classify 206 action 300c as a possible cheating event using, e.g., attention level 302c of user 48.

Additionally/alternatively, as noted above, if data anomaly detection process 10 classifies 206 action 300c as a cheating event, data anomaly detection process 10 may provide 208 alert 312 (e.g., cheat event alert 312c) of the cheating event to at least one of user 48 and a second user (e.g., user 50 via client electronic device 42).

Additionally/alternatively, data anomaly detection process 10 analyzing 204 attention level 302 of user 48 may include identifying 216 action 300 of user 48 as requiring attention level 302 of user 48 to reach a threshold attention level (e.g., control attention level 304), and determining 218 whether attention level 302 of user 48 is less than control attention level 304 for action 300 of user 48. For example, one or more actions may require all users to spend some time and attention. For instance, an action that only requires a user to know a fact may be difficult, but may not necessarily require prolonged attention. Consider for example purposes only the following two actions: (1) "What is the value of π to two decimal places?" (2) "There are 4 circles, one with radius 1 cm, one with radius 4 cm, one with radius 6 cm and one with radius 10 cm. What is the combined area of all four circles to two decimal places?"

Even if a user (e.g., user 48) were a strong mathematician, user 48 may still need to concentrate and pay attention to the second action (e.g., action 300d) to a certain threshold attention level (e.g., control attention level 304d), even if action 300d is not considered to be that of a high difficulty level 306d (e.g., 0.2). Thus, it may be useful for data anomaly detection process 10 to analyze 204 and identify 216 questions which may require a higher attention level and determine 218 whether attention level 302d of user 48 is less than control attention level 304d for action 300d. If data anomaly detection process 10 determines 218 that attention level 302d of user 48 is less than control attention level 304d for action 300d, data anomaly detection process 10 may classify 206 action 300d as a cheating event using, e.g., attention level 302d of user 48.

Additionally/alternatively, as noted above, if data anomaly detection process 10 classifies 206 action 300d as a cheating event, data anomaly detection process 10 may provide 208 alert 312 (e.g., cheat event alert 312d) of the cheating event to at least one of user 48 and a second user (e.g., user 50 via client electronic device 42).

While action 300 taken by user 48 may include the answering of one or more questions, those skilled in the art will appreciate that other tasks may be associated with action 300. For example, action 300 may include but is not limited to, performing a manual task, such as solving a puzzle, writing a document (e.g., to detect plagiarism), reading, researching, deciding which input device (e.g., keyboard) key to press, or performing any other cognitive task. As such, any particular description of action 300 being a question to answer should be taken as an example only and not to limit the scope of the disclosure.

While one or more embodiments of the disclosure is described in terms of data anomaly detection process 10 analyzing 204 brainwaves, those skilled in the art will appreciate that other biological characteristics may also be used without departing from the scope of the disclosure. For example, monitoring device 66 may include heart rate monitoring capabilities used, e.g., by data anomaly detection process 10, to determine 202 a heart rate of user 48, where the heart rate may be analyzed 204 by data anomaly detection process 10, e.g., similarly to the operation of a lie detector. As such any particular description of analyzing brainwaves should be taken as an example only and not to limit the scope of the disclosure.

Those skilled in the art will recognize that analysis 204 by data anomaly detection process 10 may include any combination of attention level 302, control attention level 304, difficulty level 306, actual time 308, control time 310, as well as other data. Therefore, any particularly described combination of analyzing 204 attention level 302, control attention level 304, difficulty level 306, actual time 308, and control time 310 should be taken as an example only and not to limit the scope of the disclosure. Further, while a table is shown in FIG. 3, this is to help in the explanation of the disclosure, and those skilled in the art will appreciate that any data format or technique may be used to maintain the information of FIG. 3. As such, the specific format of FIG. 3 should be taken as an example only and not to limit the scope of the disclosure.

Additionally/alternatively, to aid in preventing user 48 from tricking data anomaly detection process 10 (e.g., by using pre-recorded brainwaves or by tampering or otherwise disabling the monitoring device), certain protections may be used by data anomaly detection process 10. Such protections may include but are not limited to, a time system within monitoring device 66, client electronic device 40 and/or other device cooperatively ensuring proper use and function of all components, and video recording user 48 using monitoring device 66, where monitoring device 66 or other device may include an appropriate serial number shown on the video recording.

Additionally/alternatively, data anomaly detection process 10 may provide feedback to user 48 at the end of performing an action (e.g., informing user 48 which actions are right and wrong and/or giving explanatory feedback when the action is wrong). Notably, a problem may exist in giving such feedback, in that it may overload user 48 with details such that user 48 loses attention. As such, data anomaly detection process 10 may use the same or similar techniques discussed throughout to analyze 204 attention to feedback, and then to increase/decrease the amount of feedback depending on the attention level.

Additionally/alternatively, there may be a mental difference between, e.g., retrieving information from memory and getting information from some other location. For instance, a different mental signature may be produced when user 48 retrieves information from memory to answer a question, as opposed to when user 48 looks up the information in a book. As such, data anomaly detection process 10 may use the same or similar techniques discussed throughout to analyze 204 whether user 48 is retrieving information from memory to answer a question, or retrieving the information from elsewhere. As a result, data anomaly detection process 10 may distinguish between genuine answering of a question from memory and being told the answer after having looked up the answer elsewhere. Therefore, data anomaly detection process 10 may analyze 204 the attention of user 48 to be sure that the exam is really testing what is in the brain of user 48, not just what user 48 answers.

Those skilled in the art will recognize that while a single user action may analyzed to classify whether a cheating event has occurred, the cheating event may be determined by multiple user actions without departing from the scope of the disclosure. For example, the mind of user 48 may wander occasionally and may or may not be a sufficient indicator of a cheating event. As such, those skilled in the art will appreciate that one or more actions may be analyzed by data anomaly detection process 10 to determine whether a threshold of actions may be classified as a cheating event (e.g., before classifying a cheating event and/or providing an alert of the cheating event). The threshold may be adjusted, e.g., via a user interface in combination with data anomaly detection process 10, to aid in lessening the risks of a false positive of classifying a cheating event. For example, if three actions are the threshold amount of classified cheating events, then the first two actions that may be normally classified as a cheating event separately as described above may not yet be classified as a cheating event, but may merely be classified as an anomaly by data anomaly detection process 10; however, if three or more actions that may be classified as a cheating event on their own occur, then one or more of the three or more actions may be classified as a cheating event and not an anomaly. As such, the classification of an action (i.e., a single action) as a cheating event may, but need not, also include the classification of one or more actions as anomalies for at least a portion of an assessment before data anomaly detection process 10 has determined that a threshold of cheating events (or anomalies) have been classified. In the example, data anomaly detection process 10 may wait until the threshold has been reached before providing an alert as noted above. Therefore, the classification of an action (i.e., a single action) as a cheating event should be taken as an example only and not to otherwise limit the scope of the disclosure.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block(s) may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps (not necessarily in a particular order), operations, elements, and/or components, but do not preclude the presence or addition of one or more other features, integers, steps (not necessarily in a particular order), operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications, variations, and any combinations will be apparent to those of ordinary skill in the art without departing from the scope and spirit of the disclosure. The embodiment(s) were chosen and described in order to best explain the principles of the disclosure and the practical application, and to enable others of ordinary skill in the art to understand the disclosure for various embodiment(s) with various modifications and/or any combinations of embodiment(s) as are suited to the particular use contemplated.

Having thus described the disclosure of the present application in detail and by reference to embodiment(s) thereof, it will be apparent that modifications, variations, and any combinations of embodiment(s) are possible without departing from the scope of the disclosure defined in the appended claims.

What is claimed is:

1. A computer-implemented method executed by a processor comprising:
    identifying brainwaves of a user;
    determining an attention level of the user with the identified brainwaves;
    analyzing the attention level of the user; and
    classifying an action of the user as a cheating event using the analyzed attention level of the user.

2. The computer-implemented method of claim 1 wherein analyzing the attention level of the user includes comparing the attention level of the user with a second attention level, wherein the second attention level is from at least one of the user and a second user.

3. The computer-implemented method of claim 1 wherein analyzing the attention level of the user includes comparing the attention level of the user with a difficulty level of the action of the user.

4. The computer-implemented method of claim 3 wherein analyzing the attention level of the user further includes comparing an amount of time spent by the user to perform the action with the difficulty level of the action.

5. The computer-implemented method of claim 1 wherein analyzing the attention level of the user includes:
    identifying the action of the user as requiring the attention level of the user to reach a threshold attention level; and
    determining that the attention level of the user is less than the threshold attention level for the action of the user.

6. The computer-implemented method of claim 1 wherein the action of the user includes answering one or more questions.

7. The computer-implemented method of claim 1 further comprising providing an alert of the cheating event to at least one of the user and a second user.

8. A computer program product residing on a computer readable medium having a plurality of instructions stored thereon which, when executed by a processor, cause the processor to perform operations comprising:
    identifying brainwaves of a user;
    determining an attention level of the user with the identified brainwaves;
    analyzing the attention level of the user; and
    classifying an action of the user as a cheating event using the analyzed attention level of the user.

9. The computer program product of claim 8 wherein analyzing the attention level of the user includes comparing the attention level of the user with a second attention level, wherein the second attention level is from at least one of the user and a second user.

10. The computer program product of claim 8 wherein analyzing the attention level of the user includes comparing the attention level of the user with a difficulty level of the action of the user.

11. The computer program product of claim 10 wherein analyzing the attention level of the user further includes comparing an amount of time spent by the user to perform the action with the difficulty level of the action.

12. The computer program product of claim 8 wherein analyzing the attention level of the user includes:
identifying the action of the user as requiring the attention level of the user to reach a threshold attention level; and
determining that the attention level of the user is less than the threshold attention level for the action of the user.

13. The computer program product of claim 8 wherein the action of the user includes answering one or more questions.

14. The computer program product of claim 8 further comprising providing an alert of the cheating event to at least one of the user and a second user.

15. A computing system including a processor and memory configured to perform operations comprising:
identifying brainwaves of a user;
determining an attention level of the user with the identified brainwaves;
analyzing the attention level of the user; and
classifying an action of the user as a cheating event using the analyzed attention level of the user.

16. The computing system of claim 15 wherein analyzing the attention level of the user includes comparing the attention level of the user with a second attention level, wherein the second attention level is from at least one of the user and a second user.

17. The computing system of claim 15 wherein analyzing the attention level of the user includes comparing the attention level of the user with a difficulty level of the action of the user.

18. The computing system of claim 17 wherein analyzing the attention level of the user further includes comparing an amount of time spent by the user to perform the action with the difficulty level of the action.

19. The computing system of claim 15 wherein analyzing the attention level of the user includes:
identifying the action of the user as requiring the attention level of the user to reach a threshold attention level; and
determining that the attention level of the user is less than the threshold attention level for the action of the user.

20. The computing system of claim 15 wherein the action of the user includes answering one or more questions.

21. The computing system of claim 15 further comprising providing an alert of the cheating event to at least one of the user and a second user.

* * * * *